US010441772B2

(12) United States Patent
Lucas

(10) Patent No.: US 10,441,772 B2
(45) Date of Patent: Oct. 15, 2019

(54) PORTABLE, POWERED COLLECTION SYSTEM FOR FLEXIBLE FLUID HOSES

(71) Applicant: Timothy Craig Lucas, Bixby, OK (US)

(72) Inventor: Timothy Craig Lucas, Bixby, OK (US)

( * ) Notice: Subject to any disclaimer, the term of this patent is extended or adjusted under 35 U.S.C. 154(b) by 51 days.

(21) Appl. No.: 15/436,789

(22) Filed: Feb. 18, 2017

(65) Prior Publication Data
US 2017/0239011 A1 Aug. 24, 2017

Related U.S. Application Data

(60) Provisional application No. 62/297,828, filed on Feb. 20, 2016.

(51) Int. Cl.
*A61M 39/08* (2006.01)
*A61M 16/08* (2006.01)
*A61M 16/10* (2006.01)
*B65H 51/10* (2006.01)
*B65H 75/36* (2006.01)
(Continued)

(52) U.S. Cl.
CPC ........ *A61M 39/08* (2013.01); *A61M 16/0875* (2013.01); *A61M 16/101* (2014.02); *B65H 51/10* (2013.01); *B65H 75/362* (2013.01); *B65H 75/4402* (2013.01); *A61M 16/0078* (2013.01); *A61M 2202/0208* (2013.01); *A61M 2209/06* (2013.01); *A61M 2209/082* (2013.01); *B65H 2701/33* (2013.01)

(58) Field of Classification Search
CPC ........ B65H 51/10; B65H 51/12; B65H 51/28; B65H 51/30; B65H 51/32; B65H 59/06; B65H 59/20; B65H 59/24; B65H 59/28; B65H 59/30; B65H 75/40; B65H 75/406; B65H 2701/33; B65H 75/34; B65H 75/36; B65H 75/362; A61M 16/0875; A61M 39/08; A61B 2050/311
See application file for complete search history.

(56) References Cited

U.S. PATENT DOCUMENTS 2,670,926 A * 3/1954 Sewell ................... B65H 51/10
226/186
4,343,420 A * 8/1982 Scott ................... B65H 75/362
226/127
4,541,615 A 9/1985 King, Jr.
(Continued)

OTHER PUBLICATIONS

Crouzet, D.C. Motors, Jul. 4, 2004, available at http://stevenengineering.com/Tech_Support/PDFs/44MOTORS.pdf (Year: 2004).*
(Continued)

*Primary Examiner* — Michael C McCullough
(74) *Attorney, Agent, or Firm* — Rylander & Associates, PC; Philip R.M. Hunt

(57) ABSTRACT

The present invention relates generally to medical equipment, more particularly, the use of fluid hoses coupling tanks to cannulas, as part of medical gas therapy, such as oxygen therapy. The invention describes a collection system for managing excess flexible hose that a patient might need to wear for medical reasons such as home oxygen medical therapy. It comprises a collection container, a non-spooling roller system for collecting excess hose into the collection container and extraction from the collection container, and power system to power and control the roller system.

8 Claims, 4 Drawing Sheets

(51) Int. Cl.
*B65H 75/44* (2006.01)
*A61M 16/00* (2006.01)

(56) References Cited

U.S. PATENT DOCUMENTS

| | | | | |
|---|---|---|---|---|
| 4,692,569 | A * | 9/1987 | Winner | B64F 1/34 |
| | | | | 191/12 R |
| 4,739,913 | A | 4/1988 | Moore | |
| 4,853,500 | A * | 8/1989 | Tydlacka | B65H 75/362 |
| | | | | 191/12 R |
| 5,332,171 | A * | 7/1994 | Steff | B65H 75/38 |
| | | | | 242/378 |
| 6,109,544 | A | 8/2000 | Sheng | |
| 6,427,284 | B1 | 8/2002 | Harrelson, II | |
| 7,285,111 | B2 | 10/2007 | Gaster | |
| 7,487,791 | B1 | 2/2009 | Bradley | |
| 7,973,516 | B2 * | 7/2011 | Flack | B60L 11/1816 |
| | | | | 174/61 |
| 8,028,834 | B2 | 10/2011 | Lill | |
| 2005/0028493 | A1 * | 2/2005 | Small | A47L 9/0036 |
| | | | | 53/510 |
| 2006/0243282 | A1 * | 11/2006 | Sackman | A61M 16/08 |
| | | | | 128/205.22 |
| 2008/0210236 | A1 | 9/2008 | Resmed | |
| 2009/0205991 | A1 | 8/2009 | Lill | |
| 2010/0307496 | A1 * | 12/2010 | Lueckenhoff | A61M 16/0875 |
| | | | | 128/204.18 |
| 2012/0152926 | A1 * | 6/2012 | Matiash | B23K 9/1336 |
| | | | | 219/137.7 |
| 2015/0075528 | A1 | 3/2015 | Kudo | |
| 2015/0237933 | A1 | 8/2015 | Abshire | |
| 2016/0060075 | A1 * | 3/2016 | Slowik | B65H 75/4484 |
| | | | | 242/390.2 |
| 2016/0354570 | A1 * | 12/2016 | Arroyo | A61M 16/101 |

OTHER PUBLICATIONS

Lee W. Young, Written Opinion of the International Searching Authority, PCT/US2018/03422, dated Oct. 17, 2018, pp. 1-12, IPEA/USPTO, Aelxandria VA, USA.

* cited by examiner

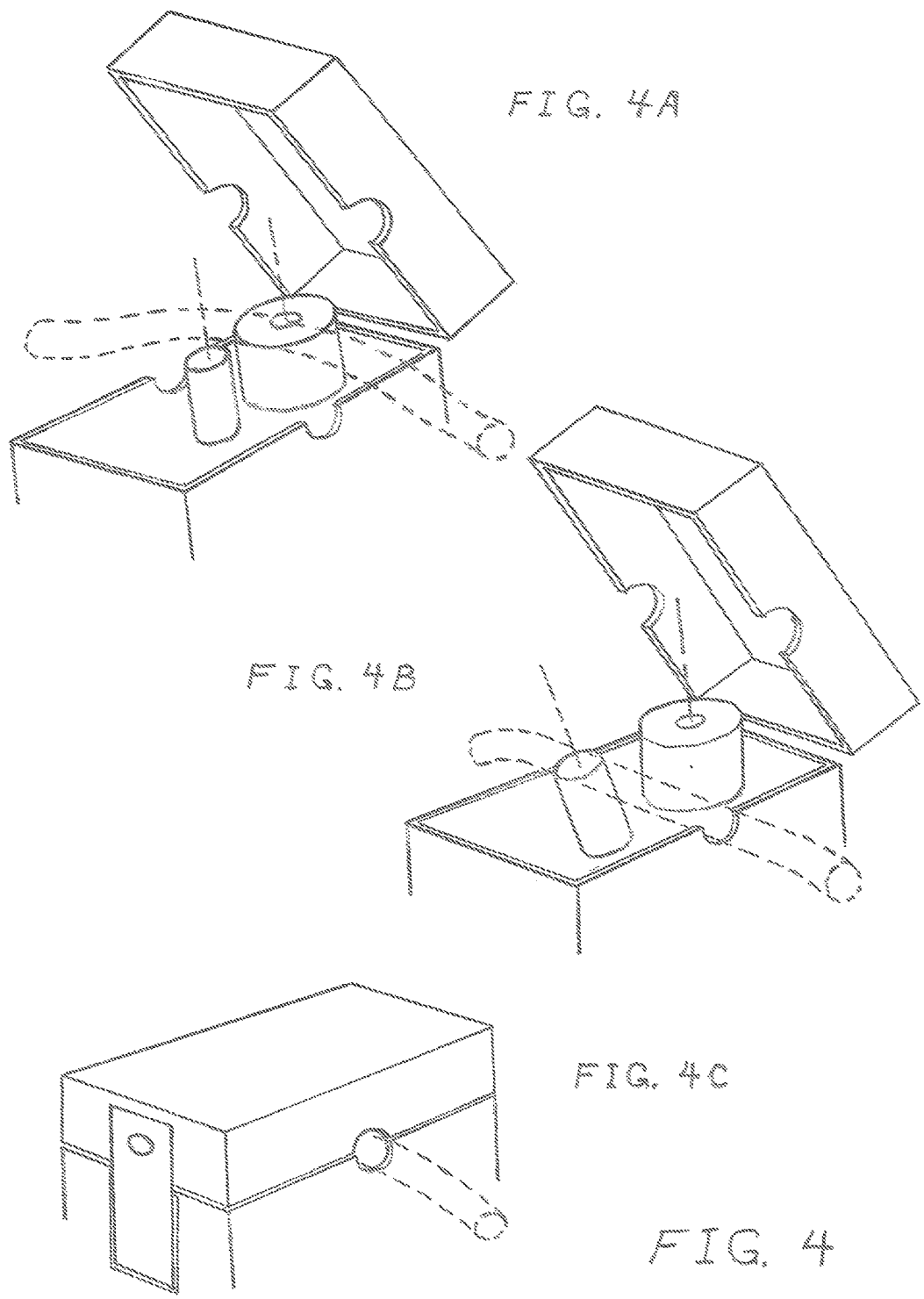

PORTABLE, POWERED COLLECTION SYSTEM FOR FLEXIBLE FLUID HOSES

CROSS-REFERENCE TO RELATED APPLICATIONS

The invention claims priority of provisional patent application No. 62/297,828, filing date Feb. 20, 2016, Flexible Tube and Hose Management System.

BACKGROUND OF THE INVENTION

Technical Field

The field of the invention is ancillary devices for patient medical care, particularly bags or receptacles for storing and carrying fluid hose.

Chronic Obstructive Pulmonary Disease (COPD) is a group of diseases—which includes emphysema and chronic bronchitis—which cause breathing-related problems and airflow restriction. According to the CDC, approximately 16 million Americans have been diagnosed with COPD (almost 7% of the population). The number of people with this condition is presumably much higher: the COPD Foundation estimated the total number affected at 30 million, which is generally in line with the NIH (which estimated 12 million undiagnosed COPD cases in 2012).

Worse yet, chronic lower respiratory disease is the third leading cause of death in the U.S., with COPD causing over half of the deaths from lung diseases. [source: NIH's National Heart Lung and Blood Institute. 2012 Morbidity and Mortality: Chart Book on Cardiovascular, Lung, and Blood Diseases. https://www.nhlbi.nih.gov/research/reports/2012-mortality-chart-book]

COPD is costly. The CDC estimated that the costs attributable to having COPD were approximately $32 billion in 2010, paid as follows: Medicare paid 51%, Medicaid paid 25% and private insurance paid 18%. "By 2020 it is expected that the cost of medical care for adults with COPD will be more than $90 billion . . . " [source: CDC website.]

For people with COPD or similar condition, oxygen therapy is often prescribed by their doctors for the related medical conditions. In fact, about 14% of patients are prescribed oxygen therapy. [source: Direct costs of chronic obstructive pulmonary disease among managed care patients, Anand A Dalal, Laura Christensen, Fang Liu, and Aylin A Riedel, Int J Chron Obstruct Pulmon Dis. 2010; 5: 341-349. https://www.ncbi.nlm.nih.gov/pmc/articles/PMC2962300]

Out of the total of $32 billion, Medicare spends a great deal on home oxygen equipment itself. According to the NIH's National Heart, Lung, and Blood Institute and the Centers for Medicare and Medicaid Services in 2004, "Total Medicare reimbursements for costs related to [oxygen therapy] exceed $2 billion/year and are increasing at an annual rate of 12 to 13%." [source: Long-term Oxygen Treatment in Chronic Obstructive Pulmonary Disease: Recommendations for Future Research, Thomas L. Croxton, William C. Bailey, American Journal of Respiratory and Critical Care Medicine Vol 174. pp. 373-378, 2006. https://www.nhlbi.nih.gov/research/reports/2006-oxygen-treatment] [Back in 1997, Medicare was spending $1.8 billion annually for home oxygen equipment for COPD, so the pace appeared to accelerate. Source: Long-Term Oxygen Therapy: New insights and perspectives, pp 221-232, Chapter 19: The Economic Impact of Long-Term Oxygen Therapy Lorenzo G. Mantovani, Marco Cristiani, Gianluca Furneri. 2012.]

The National Home Oxygen Patients Association claimed in 2012 that over one million people used supplementary oxygen, but considering an estimated 800,000 people used home oxygen in 1995; presumably, the numbers are substantially higher now [Source: O'Donohue W J and A L Plummer, Magnitude of usage and cost of home oxygen therapy in the United States, Chest 107: 301-302, 1995].

There are three common sources of medical oxygen: concentrators, compressed gas, or liquid. Patients are required to pull around a wheeled tank. Most concentrators, on the other hand, are large, stationary units.

All three require the use of oxygen tubing from the tanks or concentrator to the patient's cannula. The tubing or hose that connects to the concentrator and the patient can easily become tangled and hinder free and easy movement of the patient.

Loose hose underfoot poses a tripping threat that could lead to the patient—or others—falling. Loose hose also increases the potential of kinking, pinching, or other obstruction of the hose and its gas flow. These risks are amplified if the patient has mobility issues and/or uses a walker, cane or wheelchair in addition to medical gas therapy equipment. In hospital and at home, extra hose is sometimes looped and hung from IV stands or tank carts, or even draped over the tanks themselves, practices which have the same drawbacks.

Background Art

Some current methods to address this loose or excess hose problem are expensive and not easily maintained, nor are they easy to install or set up. They can be large and/or heavy. They are not intuitive. Some methods rely on a spool to wrap the hose around, which can lead to pinching and kinking of the hose. Spooling increases twisting of hose, by forcing it in a fixed position around a spool. Spooling methods add bulk as well because of the spool diameter. See, e.g., US Patent Application 2005/0028493 A1, published Feb. 10, 2005, from Small.

Other methods rely on ceiling mounted devices that are difficult to install and to use and maintain, and are far less mobile than a carried container. Other methods available manage excess hose by means of an accordion type jacket or gather placed around a section of the excess hose, which is an imperfect solution because of device bulk; and the device can itself become a hazard. See, e.g., US Patent Application 2015/0075528 A1, published Mar. 19, 2015, from Kudo, which shows how a gather will apply continual pressure on the patient because the device itself can create hazardous or inconvenient tension or "springiness," as noted in that application. And that type of solution can prevent the patient from using both hands for other tasks.

Another method is to use a soft-sided sack used to collect hose, such as U.S. Pat. No. 4,739,913, issued Apr. 26, 1988, to Moore and U.S. Pat. No. 8,028,834 B2, issued Oct. 4, 2011, to Lill. However, using only a flexible fabric bag leads to bunching and twisting of the hose while in the container and can lead to pinching and kinking of the hose, and which causes difficulty when extracting the hose from the bag.

Some soft-bag methods try to get around the bunching and twisting issues inherent in soft side bags by teaching using a single, typically centered, rib to provide some structure to a soft hose bag, but this solution does very little to maintain the interior volume of the collection container, other than to keep constant the distance from the bag's top to bottom.

Extraction is also an issue with soft bags, as they are particularly problematic in an emergency situation, when it's necessary to remove the hose from the bag quickly and untangle it. Anyone having to quickly pull items from a soft-sided backpack can attest to this, particularly when it's on the person's back.

Other alternative methods include hard-sided cases for hose, such as U.S. Pat. No. 7,487,791 B1, issued Feb. 10, 2009 to Bradley. This method is best suited to collecting loose hose once, but poorly suited to repeated collection and extraction because the hose is essentially clipped in place.

Further, these bagging or clipping methods do not offer functional means of collecting the hose into the bag, other than manually stuffing the hose in by hand.

The present invention seeks to offer a low cost, easy to manufacture, easy to maintain and use system that more completely manages the problem of excess hose for the patient or a person who wants to make sure hose is safely collected and not underfoot.

BRIEF SUMMARY OF THE INVENTION

The invention is a portable and wearable, self-contained, light-weight, powered system that allows a user to collect excess, loose fluid hose into a collection container and extract the hose as needed. It comprises a collection container, a non-spooling roller system powered by a small motor that can draw the excess hose into the collection container in such a way that hose remains connected to both the gas source and cannula and properly connected to the patient. In addition to allowing the patient—or another person—to collect the excess or loose hose, it allows for extraction of the hose from the collection container as needed for movement.

The invention can be used with any of the fluid or oxygen supply sources, from concentrators to tanks.

The invention comprises three basic, essential elements: a collection container, a non-spooling roller system, and a power system for collecting into and extracting hose from the collection container, and power system to power and control the roller system.

BRIEF DESCRIPTION OF DRAWINGS

Having thus described the invention in general terms, reference will now be made to the accompanying drawings, which are not necessarily drawn to scale.

Figure 1:
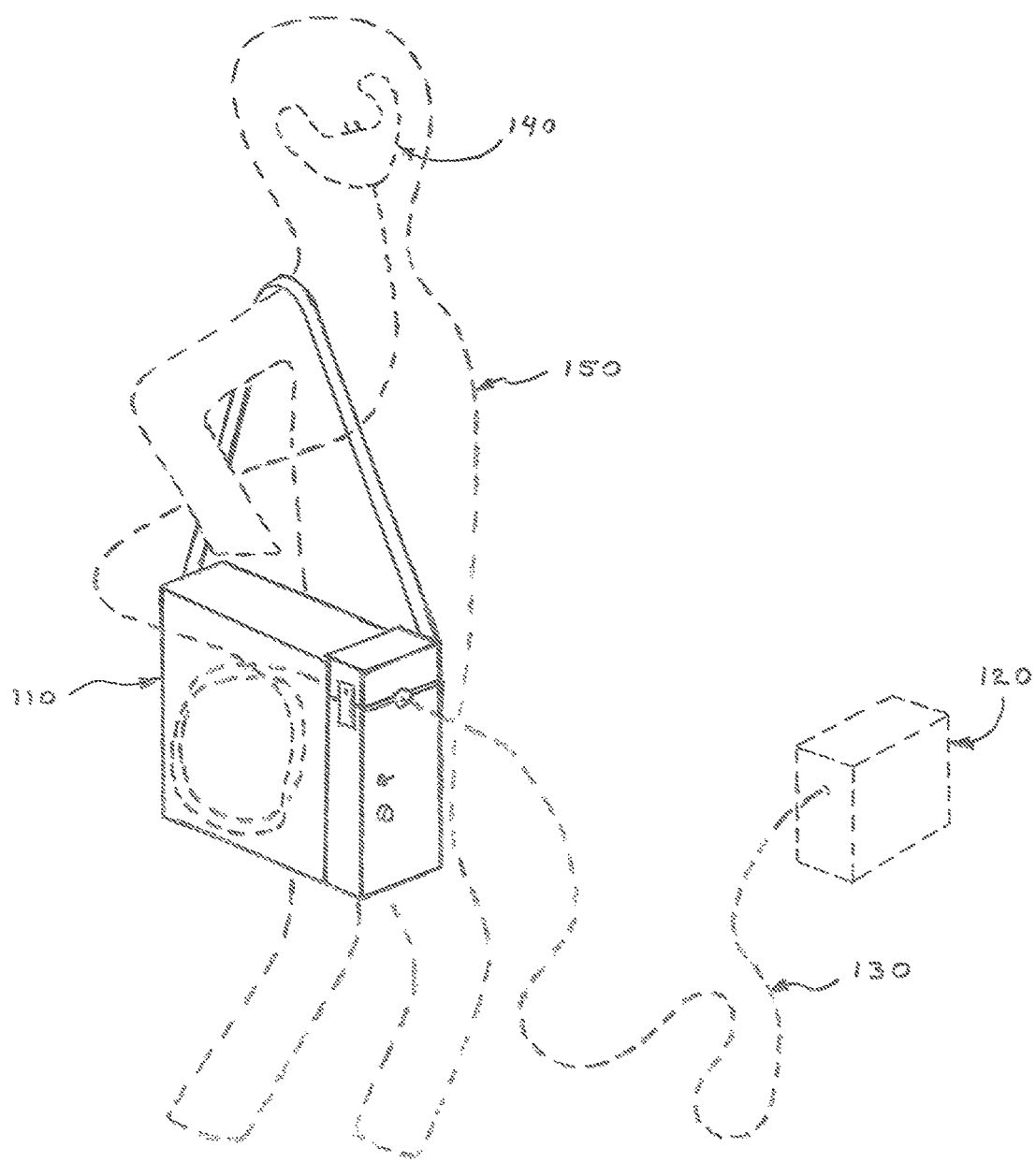

FIG. 1 shows a top, side perspective view of the invention being worn by a patient while the patient is also wearing a cannula and oxygen hose which is also connected to an oxygen concentrator.

Figure 2:
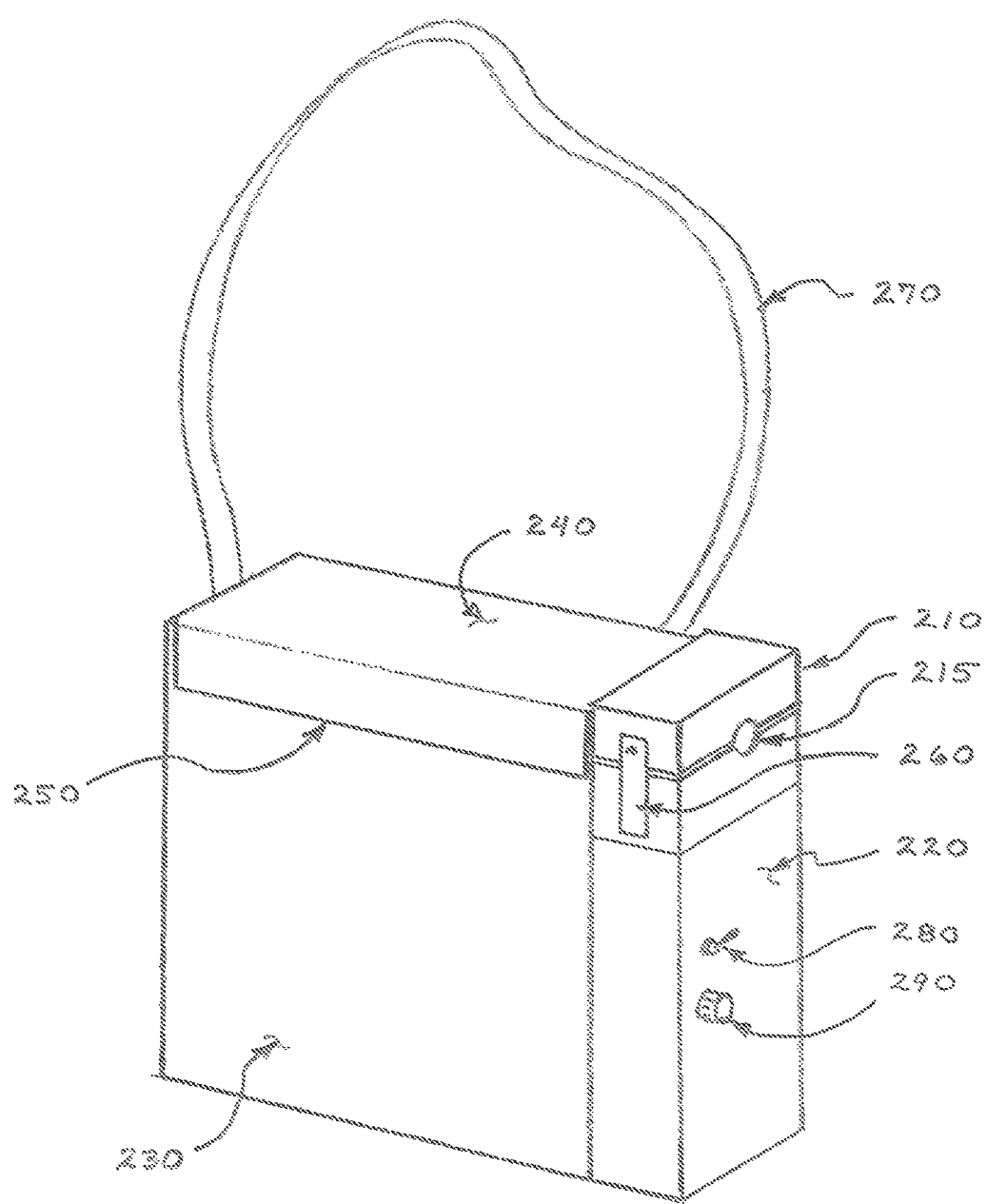

FIG. 2 shows a top, side perspective view of the invention.

Figure 3:
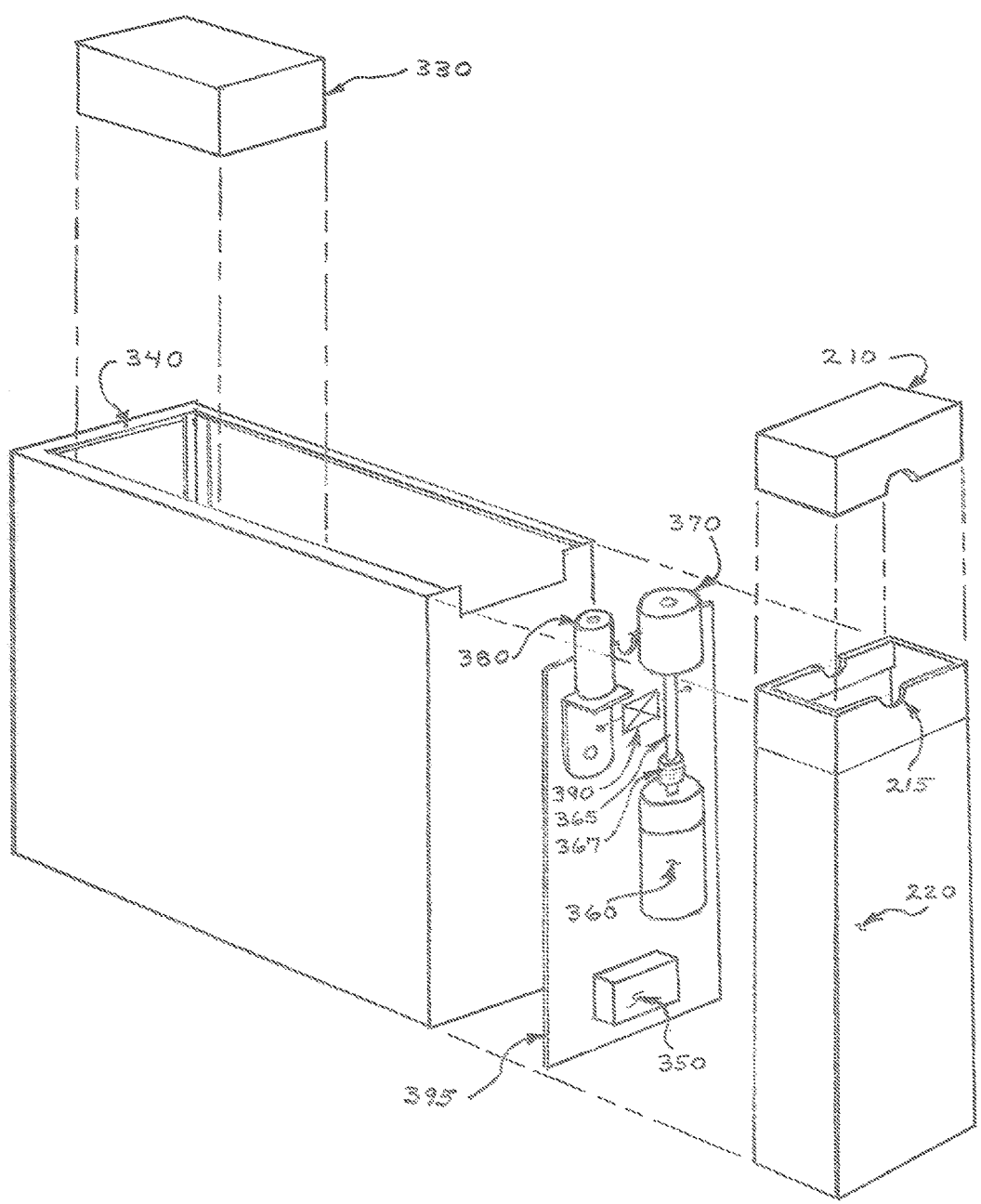

FIG. 3 shows a top, side perspective exploded view of FIG. 2.

FIG. 4 is a top, side perspective, close-up view of the roller system in two positions, FIGS. 4A and 4B, as well with the hose guide in closed position, FIG. 4C. The hose is not claimed, shown only for reference, and is shown in dashed lines.

DETAILED DESCRIPTION OF THE INVENTION

Before beginning a detailed description of the subject invention, mention of the following is in order. When appropriate, like references are used to designate identical, corresponding, or similar components in different figure drawings. The figure drawings associated with this invention are not drawn with strict dimensional accuracy, i.e., the drawings have been drafted with a focus on clarity of viewing and understanding rather than dimensional accuracy.

For all the components in this invention, it is preferable that the components be as small, light-weight, and portable as possible, taking into consideration cost of materials and manufacture. This is preferable to make the invention portable, wearable, self-contained, and light-weight, so it can be carried by a patient and be constructed using components which are cost-effective.

Referring now to the invention in more detail, FIG. 1 shows a patient 150 wearing the collection system 110. Here, as an example, an oxygen concentrator 120 has hose 130 coming out of it and running into the collection system 110 and the hose continues, up to the cannula 140 on the patient. The hose, the patient, the cannula, and the oxygen concentrator are not claimed, but are shown for reference.

There are several essential elements in the present invention. First, a collection container 230 which contains collected hose 130 (see FIG. 1). Second, a roller system which allows for collection and release of hose, in and out of the collection container, respectively. More specifically, a roller system which collects and releases hose without any spooling. Third, a power system to power the roller system and provide for variable speeds and the proper torques. The power system comprises a control system for controlling the roller system operation, a motor system, and a power supply system.

Most components of the roller system and power system are mounted to a mounting surface 395 (FIG. 3). The mounting surface is attached to the collection container's frame 340. The mounting surface could be manufactured from various rigid materials, so long as it is sufficiently rigid and strong to hold components securely in place, while being light enough to allow for convenient transport of the invention by the user. Hard plastic or aluminum are two preferred choices for materials. Alternatively, multiple mounting surfaces for component parts can be used in order to save material costs. Alternatively, one or more component mounting points can be integrated in the frame itself, if, for example, injection-molded plastic is used to construct the frame, one or more mounting surfaces or component attachment points can be formed as part of the frame.

The collection container's frame 340 is either internal or external to collection container 230 and it maintains the collection container's internal volume. As noted, the collection container is adjacent to the roller system and power system. The frame maintains the collection container's internal volume side-to-side and top-to-bottom. This prevents the aforementioned bunching, twisting, and kinking of the hose 130 while it is in the collection container, and it allows for the hose to be quickly removed from the collection container when desired, particularly in the event of an emergency.

The frame 340 offers an additional feature as it provides an anchor point for the power system, roller system, and control system, holding them adjacent to the collection container 230. This anchor point provides support for all the systems, and allows for all of the systems to work properly in conjunction with each other. As noted, the mounting surface 395 is attached to the frame. This rigid mounting overcomes problems inherent with having rollers loosely mounted and not powered, as in US Patent Application 2009/0205991 A1, published Aug. 20, 2009 from Lill. The present invention's anchoring of components permits powered operation of the rollers, sufficient friction between rollers and hose, and proper positioning between the hose and the collection container.

The power system comprises several basic elements, which can be seen in FIG. 3. First, a motor 360 which can be operated at variable speeds and reversing directions such as clockwise and counter-clockwise. Second, a power supply 330 that provides electrical current to power the motor. Third, a control system 350 that can turn the system on and off and provide variable speed and directional control over the roller system. The control system modulates the power supplied to the roller system.

The motor 360 can be one of many readily available, off-the-shelf motors and gear reducer assemblies available on the market that provide the proper torque (measured in kilogram force centimeter, kgf-cm) and sufficient speed (measured in revolutions per minute, RPM) to retract or release the hose 130 at a speed appropriate for the user to manage and control and which can be altered to suit the patient's particular movements and pacing.

The motor 360 would preferably be a small, light-weight assembly, which must be capable of reversing directions clockwise to counter-clockwise and vice versa. The preferred embodiment uses a 12V DC motor. The motor is attached to the mounting surface 395.

The preferred motor 360 has two essential characteristics in addition to expense, size, and weight. First, it must be capable of a range of speeds, preferably a range of between 0 and 1500 maximum RPMs. Lower speeds are not preferred because they are too slow for the walking pace of most patients. Higher speeds should be avoided as the increased speed of hose 130 intake could pose a safety threat to the patient. Higher speeds are also impractical because they do not represent normal walking speeds and motors producing higher speeds tend to be less available and costlier.

Second, the preferred motor 360 should be capable of operating at torques of between 6 kgf-cm and 9 kgf-cm at load, with a preferred torque of 7.9 kgf-cm at stall. Lower torques can be utilized, but there is a greater likelihood that the rollers will stall when in use. Higher torques could pull too hard on the hose 130, and this should be avoided. The required torque must be sufficiently high to facilitate intake of the hose, overcoming the weight of the hose on the floor and overcoming minor impediments to collecting the hose, but low enough to stall if significant hose obstruction occurs during collection so that the function remains harmless to the patient. For example, if the hose were wrapped around a piece of furniture, the invention should not pull so hard on the hose as to pull the patient off-balance. The complete power supply, drive and control system must be selected so that it will be tolerant of being in a stalled condition for brief periods.

In the preferred embodiment, the motor 360 is attached to the drive roller 370 through a ¼ inch aluminum shaft 365 that is connected to the motor drive shaft through any of commonly available flexible joint couplers 367. Different shaft diameters and materials may be used, depending on availability or cost. Further, a flexible joint coupling is not required, but a rigid joint would accelerate damage to the motor over time, so a flexible joint is preferred. The material used for the drive cylinder must have sufficient rigidity and strength to withstand the torque and speed requirements, and it must be reliably bonded to the metal shaft. It should be able to withstand long-term use of the device without undue wear and without declines in functionality, such as loss of grip and slippage.

The power supply 330 could be any number of readily available rechargeable DC power devices such as Li-ion batteries capable of providing the sufficient voltage to the motor and which offer reasonable ampere hours. The use of non-rechargeable power sources or electrical cords is disfavored because this would limit mobility of the user.

The power supply 330 can be placed any number of places, but is preferably located in the collection container 230 as shown in FIG. 2, and placed toward the bottom rear of the collection container, away from the motor and roller system, to better balance the carrying weight of the system as a whole. The power supply is preferably attached to the frame 340, so the power supply doesn't shift around the collection container when in use. It is connected to the motor 360 and control system 350 electronically using standard electrical wiring.

A housing 220 covers and protects the power system and its control system. This housing is preferably made of any lightweight and durable material such as metal, like aluminum, or hard plastic. The housing is attached to the mounting surface 395 through any various and common fastening means such as glue or screws. The housing should preferably also be attached to the collection container's frame 340 through similar fastening means. The housing provides some protection for the oxygen hose 130 and other system components from damage and provides some protection to the user, including risks such as a motor or power supply malfunction creating a spark, flame, or excessive heat, or injury to fingers from moving or electrified parts. It could be flame resistant or be covered with flame resistant material. The housing could be decorative as well.

Referring to FIGS. 1 and 2, roller controls, 280 and 290, should be installed in a convenient position for the person using the invention to have use thereof. The preferable placement is mounted in the housing 220, toward the front of the system, within easy reach of the patient or user.

The roller controls, 280 and 290, can be comprised of a single control with multiple functionalities, or the functionalities can be divided amongst two or more controls or switches, as shown in the Figures, labeled 280 and 290.

The first roller control controls on and off. In the preferred embodiment, it is directional, and has "off," "forward," (on) and "reverse" (on) conditions. A common 3-position toggle switch 280 is preferred for these three functionalities. While many other common devices exist that could control these features as well, they are typically more costly and complex. This is connected to the control system 350 electronically using standard electrical wiring.

The roller control system provides variable control of the roller speed as a functionality; this second roller control functionality is represented by the potentiometer 290. Because of its ubiquity, low cost, and ease of use, a potentiometer could be used for variable speed control. The potentiometer could take the form of a slide switch (not shown in the drawings) or knob/dial switch (shown as 290 in FIG. 2), as preferable examples. This is connected to the control system 350 electronically using standard electrical wiring.

In an alternative embodiment, a single potentiometer, and hence a single roller control, can be used to control on/off and speed. This is not shown in the figures. However, if a "reverse" function is missing, the user/patient would have to manually extract the hose 130. The "reverse" control in the preferred embodiment provides this functionality.

Alternatively, a single potentiometer, often called a "wigwag," not shown in the figures, could be used to on/off, control speed, and control direction, but this more complex type of potentiometer is a more expensive option and they are, in practice, harder to use by patients because the patient is more likely to accidentally change roller directions unintentionally by spinning the dial too far. For these reasons, "wig-wag" potentiometers are not as favorable generally.

In an alternative embodiment, not shown in the figures, software control or semiconductor control can be used to control the speed and/or torque, as well as the roller rotation direction. This approach would increase the cost and complexity of the invention, but could automate control to some extent. For example, electronic sensing means coupled with a Pulse Width Modulation circuit could maintain the torque of the motor 360 as it reduces the speed of the rollers 380 and 370. Similar electronic or software means could be used to control the speed while preventing a torque decrease, but these are more complicated and costlier currently.

As an alternative to being mounted on the housing, the roller control(s), 280 and 290, could alternatively be held in the user's hand, such as attached to a length of wire extended from the system or via a wireless device such as those that use common remote control or wireless technology, such as infrared, line-of-sight, Bluetooth, ultrasonic tones, or radio. These alternative embodiments are not shown in the Figures.

Referring now to FIG. 4, there are shown three top side perspective views, showing the rollers 380 and 370 in two positions, during the use of the invention.

First, hose 130 is inserted between the rollers. FIGS. 4A and 4B shows the hose guide 210 in an open position, hinged away from the housing 220. Also shown are the two rollers, an idler roller 380 and a powered roller 370. In FIG. 4A, the hose is shown, ready to be placed between the rollers, and the rollers are shown in "closed" position, meaning that the spring 390 tension has them at minimal distance between their axis centerlines. In FIG. 4B, the idler roller is shown pivoted or slid away from the powered roller, while the hose is inserted between the rollers. The user or patient would move the roller by hand, pushing against the tension, while removing or inserting the hose between the rollers.

Once the hose 130 is in place between the two rollers, as in FIG. 4B, the idler roller 380 would be allowed to move back toward the powered roller 370 and against the hose, pressing the hose between the idler roller and the powered roller, thereby gripping the hose and allowing operation of the invention.

The idler roller 380 must be pressed against the hose 130 with sufficient pressure so as to hold the hose against the powered roller 370 and create friction and torque sufficient to draw the hose into the collection container 230, but not create so much force that the hose 130 would be overly compressed and thereby restrict the proper transfer of fluid or gas through the hose.

As noted, the idler roller 380 can be moved away from the powered roller 370, or vice versa, for insertion of the hose 130. It is preferable that the idler roller is connected to a shaft which can be hinged or slid away from the powered roller, as shown in FIG. 4B. In this configuration, the roller system operates similar to capstan and pinch rollers in an audio tape deck. It is preferable to power only one of the rollers, to maximize simplicity and save on materials, weight, and manufacturing costs. Alternatively, the powered roller could be movable, with a stationary idler roller. Since this necessarily means that the movement of the powered roller will impact the motor 360 and shaft 365, this adds a level of complexity to the mounting of those components and will impact the tension needed to move the rollers together. It is therefore disfavored as an approach. Alternatively, both rollers could be movable, but this is disfavored because of the increased cost and manufacturing complexity and decreased durability overall.

A tensioner is used to push or pull the rollers together. In the preferred embodiment, a spring 390 is used to provide tension to pull the idler roller 380 toward the powered roller 370. Alternatively, a spring or springs could push the rollers together. A spring is favored due to its simplicity, cost, and ease of manufacturing. The spring should preferably be capable of providing tension of between 0.5 to 1 foot-pounds of pressure. In practice, less pressure would be unlikely to provide sufficient friction for the rollers to work adequately. More pressure and the hose 130 is threatened with becoming compressed laterally by the rollers, and the fluid flow could be choked off. The mechanism should further be designed to limit the minimum space between the rollers, so as to not put the hose at risk of being crushed and oxygen flow to the patient being cut off. This is preferably accomplished by a physical limiter, that would operate like a door stop, preventing the idler roller from getting too close to the powered roller. The limiter is not shown, but the result of this function is shown in FIG. 4A where the two rollers are not touching but at minimal distance from each other.

In the main embodiment, the idler roller 380, the powered roller 370, the spring 390, the motor 360 are all mounted to the mounting surface 395 which is covered by the housing 220 and, in turn, attached to the container frame 340. This permits less expensive construction and fewer components.

Preferably, the rollers 370 and 380 are mounted such that their spinning axes are vertical, as shown in the figures. Maintaining proper tension and friction on the hose 130 is more difficult when the rollers' axes are in a horizontal position, due mainly to gravity, so this configuration is disfavored.

The rollers 370 and 380, when viewed in cross-section or end plan, should preferably be round. They are preferably constructed as a common wheel-on-an-axle. The axle or shafts can be made of any rigid material of sufficient strength, such as steel or aluminum. The rollers are preferably not notched, concave or convex when viewed perpendicular to the longitudinal axis, as these different roller shapes make it more difficult to apply the proper pressure upon the hose 130 and maintain the proper distance between the powered 370 and idler roller 380. Further, rollers, like a sheave, which have notched, concave or convex faces are less desirable as they are less capable of accommodating hoses of various diameters.

Rollers 370 and 380 should preferably have a surface material sufficient to create friction and torque on the hose 130. The surface should have a hardness of equal to or less than Shore 70 A on the durometer scale, and preferably be made of polyurethane or rubber with sufficient thickness to meet this durometer hardness. Materials with higher durometer scale ratings could alternatively be used, but this decreases roller-to-hose friction and would therefore increase the likelihood of the hose slipping while the rollers are rotating. Alternatively, materials which are too low on the scale are disfavored because they could reduce durability of the rollers and may increase demands on the motor.

The preferred embodiment uses two rollers, but a plurality of rollers may be utilized. Using more than two rollers will increase the cost and complexity of the manufacture, and can add additional hose-to-roller friction.

FIG. 4C shows the hose guide 210 in a "shut" position, with the hose 130 sticking out, ready for system use. Note in the figures, FIG. 4A-C, that the housing and the hose guide have semi-circular cut-outs in them that receive the hose when the hose guide is closed, as in FIG. 4C. The hose guide covers the rollers when closed and protects them and the user. The hose sticks out through cut-outs 215 made by the hose guide and the housing. The hose guide should be designed, preferably hinged, so that it could be opened and closed readily to allow the user to install and uninstall the hose as desired, as shown in FIG. 4. FIG. 4C shows a preferred closure mechanism 260 used to hold the hose guide in the "shut" position.

The hose guide 210 and housing cut-outs 215 shown in the figures limit kinking of the hose 130 upon intake and release, as well as preventing the hose from escaping its proper position between the rollers while the rollers are in operation. As such, as shown in the drawings, the placement of the cut-outs should be at the same vertical height as the rollers so that the hose stays in between the rollers. The cut-outs keep the hose in proper horizontal and vertical alignment as it is traveling between the rollers, which helps to maintain proper contact with the rollers and hose. The hose guide is preferably connected to the housing using a common hinge so it does not come completely detached when opened.

Note that the semi-circular cut-outs 215 are on both sides of the roller system. The dimensions of the cut-outs in the hose guide 210 is dependent on the diameter of the hose 130 that the invention is designed for. The cut-out's diameter must be sufficiently wide enough and its edges must be sufficiently rounded so as to prevent cutting or scraping of the hose when used. The cut-out's dimension must be wide enough to accommodate hoses of various diameters, but not be overly wide, such that it does not allow kinked hose to enter the hose guide 210 and does not allow the hose to escape its proper position between the rollers. The cut-out should preferably be a minimum of 8 mm in diameter to accommodate the most common oxygen hoses.

The hose guide 210 could be of many different materials but with the rigidity to keep the hose straight and unkinked as it was drawn into or released from the collection container 230. Rigid plastic is used in the preferred embodiment, because of its weight, durability, cost, and ease of manufacture.

While the main embodiment uses a simple cut-out 215 in the hose guide 210 to provide the recommended unkinking and straightening of the hose and maintain the hose 130 alignment between the rollers, other alternative, but more complex, methods may be used to straighten and unkink hose. An additional element could be designed and used, such as a pulley or set of pulleys or other mechanical hose guide, like a sheave.

FIG. 3 shows a top side exploded perspective view of the collection system 110, with individual elements shown. For ease of viewing, the top of the collection container is not shown, as it is in FIGS. 1 and 2.

The collection container 230 itself can be either generally like a bag, that is, flexible, or it can be like a box, that is, rigid. The collection container should be as light as possible, so it is preferred to manufacture it as a bag constructed out of flexible material with a frame 340, rather than using rigid materials for the bag.

Preferably, then, the collection container 230 comprises two parts, a flexible bag, 230 and a frame 340. The frame is used to maintain the container's interior volume, preventing it from flattening, so as to allow the hose 130 to readily enter the bag. A common "messenger" style bag is the simplest, most easily and cheaply manufactured, and lightest configuration for the bag. The frame is attached to the bag and can either be outside the bag or inside the bag, so long as it generally maintains the shape of the bag and prevents it from collapsing.

The frame and the bag need not be square as shown in the figures and the dimensions can vary, so long as the width side-to-side and length end-to-end permit comfortable carrying by a patient, as shown in FIG. 1. No particular dimensions are essential, so long as the bag provides sufficient volume to receive the length of hose used by the patient. However, for a standard length of 50 feet of hose, which is most commonly prescribed by doctors and used by patients, the preferred but not essential dimensions of the bag in a rectangular construction should be 3.5 inches for side-to-side dimensions; the end-to-end length of 13.5 inches; and the vertical height of 12 inches. Significantly smaller dimensions will inhibit safe collection of hose as well as impair smooth functioning of the device due to over-filling of the bag with too much hose. Significantly larger dimensions will unnecessarily burden the patient with extra size and weight and limit portability. Round bags typically create unnecessary lateral bulk for the user and round bag sides complicate the mounting of mechanical components.

Having the collection container spread and held open and uncollapsed is preferable because it allows the hose 130 to more readily enter the container while being collected and allows it to remain unkinked and untangled when in the container. Having the hose unkinked and untangled while in the collection container also facilitates extraction of the hose. The frame 340 will keep the collection container from collapsing and near or at full volume at all times, even if there is no hose inside. This allows the hose 130 to more freely collect inside the collection container as it is retracted. Preventing kinking and bending are critical because the hose remains in use when the hose is stored in the collection container; oxygen must continue to flow.

The frame 340 could be constructed out of various materials such as plastic or wire, so long as the material provides enough rigidity to keep the collection container 230 from collapsing on itself, or springing back open after being compressed. The frame also allows the hose to be extracted without becoming entangled. The frame also serves as an anchoring point for the mounting surface to be connected to the collection container. The use of the frame in the present invention is a functionally superior improvement to the prior art in that the frame maintains an interior volume for the hose that prevents kinking and bending of the hose.

The collection container 230 must have an opening (not shown) that would allow the hose 130 to pass through to the patient wearing the invention, as shown in FIG. 1, without the need for extra attachments to the patient's hose.

The invention is designed so that the user could reverse the motor and extract the hose 130 while moving, by reversing the motor's direction, using the toggle switch 280. However, if the person using the invention requires the collected hose to be extracted quickly for the purpose of walking or traveling, the person could simply grasp the hose and pull the hose out upward from between the rollers and out from the collection container 230, once the hose guide 210 and the collection container top were open. This would allow the hose to be extracted with relatively little resistance. Alternatively, the user could manually draw out the hose without opening the hose guide, but the rollers and connected motor will create some resistance to this method of extracting the hose.

The top cover 240 of the collection container 230 and the hose guide 210 should each be closed using fasteners which can be rapidly opened. A simple fastener or closure 260 is shown for the hose guide in FIGS. 2 and 4. For cost and simplicity, they would preferably be comprised of Velcro-style closures or common fabric straps with snaps.

Preferably, as shown in FIG. 2, the top cover of the bag would be a flexible flap 250 like on a messenger bag. FIG. 2 also shows a carry strap 270 for the invention, which is the preferable means of carrying the invention. The carry strap is preferably attached to the frame 340 of the collection container 230, preferably using rivets or a common carabiner-style clip-and-loop system, like on common backpacks. Any durable, flexible material for the carry strap can be used, such as, for example, leather, nylon webbing, or Cordura brand fabric. Attachment to the frame is preferable because of its durability, as opposed to, for example, sewing to the fabric of the collection container.

All of the aforementioned components could be of various sizes and of various substance and material and attached in such a way that would allow them to appropriately perform the required functions as described. For instance, the rollers may need to be mounted with hubs that have ball bearings or other methods that allow smooth and unhindered rotation. Various lubricants may need to be applied at various points and places in all component configuration and interaction for proper function and behavior. These issues and methods would be obvious to one of ordinary skill.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

Multiple further embodiments can be created by variously eliminating or adding any individual, non-essential element mentioned above.

What is claimed is:

1. A lightweight and portable non-spooling fluid hose collection system, comprising:
    a collection container having a frame that maintains an interior volume of the collection container, the collection container having a first opening configured for a hose to pass through;
    a rigid mounting surface coupled to the collection container frame;
    a motor coupled to said rigid mounting surface;
    a drive roller with a drive shaft coupled to the motor, the drive roller with a driver roller axis that is vertical, the drive roller positioned above the motor;
    an idler roller with an idler roller shaft pivotally mounted to the rigid mounting surface, the idler roller with an idler roller axis that is vertical when the idler roller is in a closed position;
    a tensioner coupled to the idler roller and to the rigid mounting surface, the tensioner configured to apply force to the idler roller in a direction of the drive roller;
    wherein the idler roller is adjacent but not touching the drive roller are when the idler roller is in the closed position;
    wherein the idler roller is pivoted away from the drive roller when the idler roller is in an open position;
    a power system comprising a portable power supply that is electrically connected to the motor; and
    a control system that controls the motor.

2. A hose collection system, as in claim 1, further comprising:
    a physical limiter configured to prevent the drive roller and the idler roller from touching.

3. A hose collection system, as in claim 1, further comprising:
    a housing coupled to the frame, the housing partially covering the idler roller and the drive roller, the housing with a first semi-circular cut-out;
    a hose guide detachably coupled to the housing, the hose guide partially covering the idler roller and the drive roller when the hose guide is in a shut position, the hose guide with a second semi-circular cut-out; and
    wherein the first semi-circular cut-out and the second semi-circular cut-out align to make an entry hole, the entry hole in vertical alignment with the idler roller and the drive roller.

4. The hose collection system, as in claim 3, further comprising:
    a hinge coupled to the housing and to the hose guide, configured to allow the hose guide to detach and swing away from the housing, exposing the idler roller and the drive roller.

5. A lightweight and portable non-spooling fluid hose collection system, comprising:
    a collection container having a frame that maintains an interior volume of the collection container, the collection container having a first opening configured for a hose to pass through;
    a rigid mounting surface coupled to the collection container frame;
    a motor coupled to said rigid mounting surface;
    a drive roller with a drive shaft coupled to the motor, the drive roller with a driver roller axis that is vertical, the drive roller positioned above the motor;
    an idler roller with an idler roller shaft slidingly mounted to the rigid mounting surface, the idler roller with an idler roller axis that is vertical when the idler roller is in a closed position;
    a tensioner coupled to the idler roller and to the rigid mounting surface, the tensioner configured to apply force to the idler roller in a direction of the drive roller;
    wherein the idler roller is adjacent but not touching the drive roller are when the idler roller is in the closed position;
    wherein the idler roller is moved away from the drive roller when the idler roller is in an open position;
    a power system comprising a portable power supply that is electrically connected to the motor; and
    a control system that controls the motor.

6. A hose collection system, as in claim 5, further comprising:
    a physical limiter configured to prevent the drive roller and the idler roller from touching.

7. A hose collection system, as in claim 5, further comprising:
    a housing coupled to the frame, the housing partially covering the idler roller and the drive roller, the housing with a first semi-circular cut-out;
    a hose guide detachably coupled to the housing, the hose guide partially covering the idler roller and the drive roller when the hose guide is in a shut position, the hose guide with a second semi-circular cut-out; and
    wherein the first semi-circular cut-out and the second semi-circular cut-out align to make an entry hole, the entry hole in vertical alignment with the idler roller and the drive roller.

8. The hose collection system, as in claim 7, further comprising:
a hinge coupled to the housing and to the hose guide, configured to allow the hose guide to detach and swing away from the housing, exposing the idler roller and the drive roller.

\* \* \* \* \*